United States Patent [19]

Brown et al.

[11] 4,372,884

[45] Feb. 8, 1983

[54] PHARMACEUTICALLY ACTIVE PEPTIDES

[75] Inventors: Marvin R. Brown, San Diego; Jean E. F. Rivier; Wylie W. Vale, Jr., both of La Jolla, all of Calif.

[73] Assignee: The Salk Institute For Biological Studies, San Diego, Calif.

[21] Appl. No.: 675,149

[22] Filed: Apr. 8, 1976

Related U.S. Application Data

[63] Continuation-in-part of Ser. No. 602,259, Aug. 6, 1975, abandoned.

[51] Int. Cl.³ .......................................... C07C 103/52
[52] U.S. Cl. .............................................. 260/112.5 S
[58] Field of Search ................................ 260/112.5 S

[56] References Cited

U.S. PATENT DOCUMENTS

| | | | |
|---|---|---|---|
| 3,842,066 | 10/1974 | McKinley et al. | 260/112.5 S |
| 3,842,067 | 10/1974 | Sarantakis | 260/112.5 S |
| 3,882,098 | 5/1975 | Sarantakis | 260/112.5 S |
| 3,896,105 | 7/1975 | Chai et al. | 260/112.5 S |
| 3,904,594 | 9/1975 | Guillemin et al. | 260/112.5 S |
| 3,917,581 | 11/1975 | Immer et al. | 260/112.5 S |
| 3,931,140 | 1/1976 | Sarantakis | 260/112.5 S |
| 4,011,207 | 3/1977 | Sarantakis | 260/112.5 S |
| 4,012,345 | 3/1977 | Sarantakis | 260/112.5 S |
| 4,087,390 | 5/1978 | Shields | 260/112.5 S |
| 4,093,574 | 6/1978 | Shields | 260/112.5 S |

OTHER PUBLICATIONS

Biochem. and Biophysical Research Comm. 65, (1975), 746–750.

*Primary Examiner*—Delbert R. Phillips
*Attorney, Agent, or Firm*—Fitch, Even, Tabin, Flannery & Welsh

[57] ABSTRACT

Various peptides are described which inhibit the secretion of growth hormone by the pituitary gland and inhibit the release of glucagon and insulin by the pancreas.

42 Claims, No Drawings

PHARMACEUTICALLY ACTIVE PEPTIDES

The present application is a continuation in part of application Ser. No. 602,259, filed Aug. 6, 1975, now abandoned.

The present invention relates generally to peptides having inhibitory influence on the (1) secretion of growth hormone by the pituitary gland, (2) secretion of glucagon and insulin by the pancreas, and (3) secretion of vasoactive intestinal polypeptide, secretin, gastrin and gastric acid secretion, in humans and animals. More particularly, the present invention is directed to peptides which are effective to inhibit the release of growth hormone by the pituitary gland and to inhibit the release of glucagon and insulin by the pancreas.

A peptide having inhibitory effect on the secretion of growth hormone has been characterized and is described in U.S. patent application Ser. No. 478,175, filed June 12, 1974, now U.S. Pat. No. 3,904,594. This peptide has been named "somatostatin". Somatostatin is a tetradecapeptide and has the following structure, with the amino acid moieties numbered from left to right in accordance with usual nomenclature:

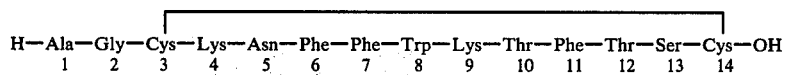

Somatostatin, the linear form of somatostatin, (dihydrosomatostatin) and various acylated derivatives of somatostatin and dihydrosomatostatin are described in the aforementioned U.S. patent application. The present invention relates to the discovery that certain amino acids can be substituted for amino acid substituents in the backbone of somatostatin and dihydrosomatostatin to provide peptides which are therapeutically valuable when introduced, either directly or indirectly, into the blood stream of mammals to inhibit the secretion of growth hormone from the pituitary gland and insulin and glucagon from the pancreas. The peptides may be introduced indirectly into the blood stream, nasally, by implanting the peptides subcutaneously or intramuscularly or by any other known methods either with or without the presence of a diluent or carrier. The peptides may be introduced directly into the blood stream by injection. Various peptides of the present invention have been found to have a potency several times greater than that of somatostatin when used for the purpose of inhibiting growth hormone, insulin and glucagon.

The principal object of the present invention is to provide peptide materials which have an inhibitory effect (1) on the secretion of growth hormone by the pituitary glands and (2) on the secretion of glucagon and insulin by the pancreas of mammalians, including humans. Another object of the present invention is to provide peptides which influence the secretion of thyroid stimulating hormone in mammalians, including humans.

These and other objects of the present invention will become more apparent from the following detailed description.

Generally, in accordance with the present invention peptides having the following structure have been found to be biologically active to inhibit secretion of growth hormone:

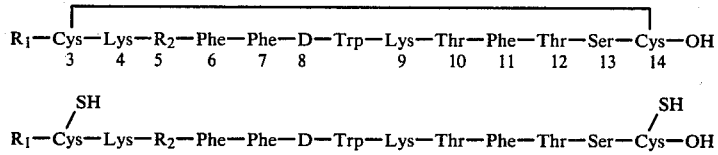

where $R_1$ is an acyl group or hydrogen and $R_2$ is selected from Ala, Asn, and des $R_2$. It has been determined that Tyr can be substituted for either or both of the Phe located at the 7 and 11 positions without influencing the effectiveness of the peptides. Also, it has been discovered that Ala can be substituted for any amino acid substituent of the above described peptides.

Preferred acyl groups which have been found to be functional for $R_1$ in the above described peptides are selected from the following: (a) des-Ala-Gly. When $R_1$ is des-Ala-Gly, $Cys^3$ can be des-amino Cys; (b) Any amino acid. For the bridged peptides, it is preferred that the amino acid does not contain a sulfhydryl group; (c) a dipeptide produced from any two amino acids wherein the second amino acid connected to $Cys^3$ does not contribute steric hindrance. Preferred second amino acids are Gly, Ala and D-Ala. For the bridged peptides, it is preferred that the amino acids of the dipeptides do not contain a sulfhydryl group; (d) A tripeptide wherein the third amino acid connected to $Cys^3$ does not contribute steric hindrance and wherein the remaining two amino acids are any amino acids. Preferred third amino acids for the tripeptide are Gly, Ala and D-Ala. For bridged peptides it is preferred that none of the amino acids of the tripeptide contain a sulfhydryl group; (e) a pentapeptide wherein the first three amino acid components are Gly, the fourth amino acid is selected from Ala and D-Ala and the fifth amino acid connected to $Cys^3$ does not contribute steric hindrance and is selected from Ala, Gly and D-Ala; (f) Aliphatic, aromatic, and cyclic organic acids, other than amino acids, having from 1 to 10 carbon atoms. The organic acids can be saturated and/or can contain other functional groups. Particularly preferred acyl groups are selected from the following: Gly, Ala, Ala-Gly, Acetyl-Ala-Gly, Tyr-Gly, Sarc-Gly, Tyr-Ala-Gly, Ala-Tyr-Gly, Acetyl, Acryl, Pivalyl and Benzoyl.

Except for the use of D-Trp, each of the amino acids in the portion of the peptides of the present invention extending between and including the two Cys groups, i.e., the 3 through 14 positions, is the L-isomer where the amino acid has isomeric forms. Any amino acid which comprises either of the R groups of the peptides of the present invention may be either the L-isomer or the D-isomer where the amino acid has isomeric forms.

A preferred peptide with high potency is provided when D-Ala is the amino acid of $R_1$ which is connected to $Cys^3$.

Surprisingly, substitution of D-Trp for Trp at the 8 position provides peptides having potencies several times greater than somatostatin in respect to growth hormone inhibition and also in respect to glucagon and insulin release. The substitution of Ala for various amino acids in the backbone of somatostatin also provides peptides with significant pharmaceutical activity.

The peptides of the present invention were synthesized by solid phase techniques, generally in accordance with the procedure described in U.S. patent application Ser. No. 478,175, now U.S. Pat. No. 3,904,594. The synthesis was conducted in a stepwise manner on chloromethylated resin. The resin was composed of fine beads (20–70) microns in diameter of a synthetic resin prepared by copolymerization of styrene with one to two percent divinylbenzene. The benzene rings in the resin were chloromethylated in a Friedel-Crafts reaction with chloromethyl methyl ether and stannic chloride. The chlorine thus introduced is a reactive benzyl chloride type of linkage. The Friedel-Crafts reaction is continued until the resin contains 0.5 to 2 millimoles of chlorine per gram of resin. In the further description of the synthesis of the peptides, the reagents used will be first described by their chemical name with their common abbreviation in parenthesis. Thereafter, the reagent will be referred to by the common abbreviation A peptide having the structure:

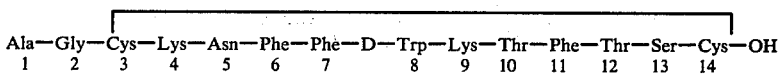

Ala—Gly—Cys—Lys—Asn—Phe—Phe—D—Trp—Lys—Thr—Phe—Thr—Ser—Cys—OH
 1    2    3    4    5    6    7     8    9    10   11   12   13   14 was synthesized by the following solid phase methodology. Other peptides, described hereinafter were synthesized by a similar technique.

The tertiobutyloxycarbonyl-S-paramethoxybenzyl (Boc-SpOMe-Bzl) derivative of Cys was linked to the resin by any of three known methods; (1) reflux in ethanol in presence of triethyl amine, (2) Cesium salt of the Boc protected amino acid is kept at 50° C. in dimethylformamide (DMF) overnight, (3) the potassium salt of the Boc-protected amino acid is kept at 80° C. in dimethyl sulfoxide (DMSO) for 2 hours. Only one milliequivalent of the protected Cys per milliequivalent of Cl on the resin is used. Method (3) is described hereinbelow in more detail; to a slurry of the resin and the dissolved protected Cys in DMSO is added 0.9 mEq of potassium tertiobutoxide (KOtBut) per mEq of amino acid. The reaction mixture is exposed to air as little as possible so that no amber coloration is observed. Reaction at 80° C. for 2 hours yields a suitable substituted resin for synthesis of the peptides (approx. 0.2 meq of amino acid derivative per g of resin). After deprotection and neutralization, the peptide chain is built on the resin. Deprotection, neutralization and addition of each amino acid is performed in accordance with schedule I. $N^\alpha$ -*t-butyloxycarbonyl (Boc) derivative of each amino acid is used with the exception that any α-amino protecting group can be used for the alanine* 1 residue (benzyloxycarbonyl; Z; Boc and others). After deprotection of the first residue (i.e., SpOMe Bzl Cys) according to schedule I (steps 3 to 8 included), the $N_{60}$ Boc derivative of Ser is next added along with a coupling agent which is dicyclohexylcarbodiimide (DCC) (step 9 of schedule I). The side chain of Ser is protected with benzyl ether (OBzl). The O-Benzyl (OBzl) protecting group is also used for protection of threonine.

P-nitrophenyl ester (ONp) was used to activate the carboxyl end of Asn. O-nitrophenyl ester can also be used for this purpose. Formyl groups can be used for the protection of the indole N-H. Benzyloxycarbonyl (Z) or benzyloxycarbonyl-2Cl [Z (2-CL)] was used as the protecting group for the Lys side chain. The $N^\alpha$ *protecting group for the last amino acid applied to the peptide can be any oxycarbonyl, such as Boc or Z. When the $R_1$* group of the peptide is an organic acid, the organic acid is attached to the peptide before the peptide is cleaved from the resin. The organic acid is attached to the peptide on the resin by introducing the organic acid in the presence of DCC or the organic anhydride or the organic active ester. The organic acid can also be added by using the organic acid as an $N^\alpha$ *protecting group for the last amino acid added.*

I.
Schedule for coupling of amino acids other than Asn in solid phase synthesis (5–10 g resin)

| Step | Reagents and operations | Mix times min. |
|------|-------------------------|----------------|
| 1 | $CH_2Cl_2$ wash 80 ml (2 times) | 3 |
| 2 | Methanol (MeOH) wash 30 ml (2 times) | 3 |
| 3 | $CH_2Cl_2$ wash 80 ml (3 times) | 3 |
| 4 | 50 percent trifluoroacetic acid (TFA) containing 5 percent 1,2-ethanedithiol in $CH_2Cl_2$ 70 ml (2 times) | 10 |
| 5 | $CH_2Cl_2$ wash 80 ml (2 times) | 3 |
| 6 | Triethylamine ($Et_3N$) 12.5 percent in $CH_2Cl_2$ 70 ml (2 times) | 5 |
| 7 | MeOH wash 40 ml (2 times) | 2 |
| 8 | $CH_2Cl_2$ wash 80 ml (3 times) | 3 |
| 9 | Boc-amino acid (10 mmoles) in 10 ml DMF (1 times) and 30 ml $CH_2Cl_2$ plus DCC (10 mmoles) in $CH_2Cl_2$ (2 M) | 30 to 120 |
| 10 | MeOH wash 40 ml (2 times) | 3 |
| 11 | $Et_3N$ 12.5 percent in $CH_2Cl_2$ 70 ml (2 times) | 3 |
| 12 | MeOH wash 30 ml (2 times) | 3 |
| 13 | $CH_2Cl_2$ wash 80 ml (2 times) | 3 |

After step 13, an aliquot is taken for a ninhydrin test:
if the test is negative, go back to step 1 for coupling of the next amino acid; if the test is positive or slightly positive, go back to steps 9 through 13. Schedule I was used for coupling of each of the amino acids of the peptide to Cys with the exception of Asn, when present. For Asn, steps 1 through 8 are the same and schedule II is used for the remainder of the coupling reaction:

II.
Schedule for Boc-Asn-ONp or for any active ester coupling in solid phase synthesis (5–10 g resin)

| Step | Reagents and operations | Mix times min. |
|------|-------------------------|----------------|
| 9 | DMF wash 60 ml (3 times) | 3 |
| 10 | Boc-Asn-ONp (15 mmoles) in 20 ml DMF (1 time) | 800 |
| 11 | MeOH wash 30 ml (4 times) | 3 |
| 12 | $Et_3N$ 12.5 percent in DMF 30 ml (2 times) | 3 |
| 13 | MeOH wash 30 ml (2 times) | 3 |
| 14 | $CH_2Cl_2$ wash 80 ml (3 times) | 3 |

After step 14, an aliquot is taken for a ninhydrin test:
if the test is negative go back to step 1 for coupling of the next amino acid; if the test is positive or slightly positive, go back to steps 9 through 14.

Cleavage of the peptides from the resin (5 grams) and deprotection of the side chain protecting groups of the peptide was performed in hydrofluoric acid (75 ml) in the presence of anisole (8 ml). After elimination of hydrofluoric acid under high vacuum, the resin-peptide was washed with ether.

The dried resin was immediately extracted with 25% acetic acid (150 ml) and diluted to 3000 ml with degassed $H_2O(N_2)$. The pH of the solution was adjusted to 6.6–7.0 with $NH_4OH$. The solution was titrated dropwise under stirring with potassium ferricyanide solution (1 g/500 ml $H_2O$) until a permanent yellow color was observed. The solution sat for 10 minutes and pH was adjusted to 5.0 with glacial acetic acid; Bio Rad AG 3-X4A resin (100–200 mesh, chloride form, 10–15 g) was added to the turbid solution and stirred for 15 minutes. The solution was filtered over celite and applied successively onto two columns; (a) Bio Rad AG 3-X4A resin chloride form (10 ml); (b) Bio Rex-70 resin (100 ml) cation form. The celite + resin cake was thoroughly washed with water (500 ml) which was applied onto columns (a) and (b) as a wash. The peptide material was then eluted from the Bio Rex- 70 resin column with pyridine:acetic acid:water (30:4:66) or 50% acetic acid. Fractions were collected; only the ones containing peptide (ninhydrin positive) were diluted with water and immediately lyophilized. 1.2 g of crude cream colored material was obtained. It was applied onto a Sephadex G-25 F gel column (3×200 cm) equilibrated and eluted with 2 N acetic acid.

The elution pattern as observed at 280 nm showed one major symmetrical peak centered at 2 $V_o$ (260 mg). It was subsequently applied onto a partition column 1.8×100 cm (n-butanol:acetic acid:water, 4:1:5). The elution pattern (280 nm) showed one major peak from $V_o$ 2.5–4.0. Two cuts were made which subsequently appeared to be identical on tlc (165 mg) (approximately 80% pure). This material (150 mg) was applied in 0.1 M $NH_4OAc$ pH 7.0 onto a CMC column (4.5×1 cm; 5 ml) and eluted with 0.2 M $NH_4OAc$ pH 7.0. Purification on CMC eliminates the tailing impurities often observed on tlc for synthetic peptides. The desired product eluted as a very narrow band which after 2 lyophilizations gave a white fluffy powder (115 mg). A minor (less than 5%) impurity running in front of D-Trp[8]-somatostatin was observed when applied on silica gel plates (Eastman 6061) and run with the upper phase of a Butanol:acetic acid:water (4:1:5) (BAW) system. This material (100 mg) was applied on a partition column 1.8×100 cm. The elution pattern (280 nm) showed one peak centered at 3.3 $V_o$. 65 mg of homogeneous material was obtained after lyophylization.

The specific optical rotation $[\alpha]_D^{23} = -47.3 \pm 0.5$ (c=1 in 1% acetic acid) is quite different from that of somatostatin $[\alpha]_D^{23} = -33 \pm 0.5$ under the same conditions. The peptide is 8 times more potent than somatostatin when used to inhibit the release of growth hormone by pituitary cells put in culture or to inhibit the arginine induced release of insulin and glucagon by the pancreas.

Active esters can be used in solid phase synthesis and the classical method of synthesis can also be used to prepare the peptides of the invention.

An in vitro assay of the effectiveness of somatostatin peptides to inhibit the release of growth hormone has been devised. The assay is made by treating pituitary glands removed from rats to separate cells therefrom. The cells are placed in culture dishes in Dulbecco's Modified Eagle Medium (Dulbecco et al., *Virology*, Vol. 8, p. 396, 1949). Carbon dioxide gas and oxygen are supplied to the cell cultures which are maintained at 37° C. for 4–5 days prior to use in the assey. Following media changes, cell cultures incubated for a period of 4 hours and particular somatostatin peptides are added thereto. Radioimmunoassay analysis is used to determine the rate of growth hormone secretion which is expressed in nanograms per hour.

The peptides of the invention inhibit basal and stimulated insulin and glucagon secretion in mammals, including humans, dogs and baboons. The peptides also inhibit insulin and glucagon release from the perfused rat pancreas, isolated islet cells and primary cultures of enzymatically dispersed pancreatic cells in vitro. It is believed that the peptides have a direct effect on the $\alpha$ and $\beta$ pancreatic cells to inhibit insulin and glucagon release.

An investigation of the effect of somatostatin, dihydrosomatostatin, (as controls) and the peptides of the invention to inhibit the release of glucagon and insulin was made as follows:

Male Sprague-Dawley rats, weighing 180–220 g., housed in temperature and humidity controlled quarters with 14 hours of light and 10 hours of dark (light 0700–2100) were used in all experiments. The animals were fed and watered ad lib. Experiments were carried out at least five days after arrival of rats from the supplier between the hours of 1400 and 1600. After ether anesthetization peptides or saline were administered in a volume of 0.2 ml via the external jugular vein followed immediately by a 1 ml bolus of arginine. Five minutes later trunk blood was collected by rapid decapitation. Plasma insulin and glucagon determinations were made by specific radioimmunoassays. Potency values relative to somatostatin (100%) were determined by four and six point bioassays.

Arginine, when administered at a dose of 100 mg/100 g BW significantly increases both insulin and glucagon release. Somatostatin and dihydrosomatostatin inhibit arginine induced insulin and glucagon release in a dose dependent equipotent manner (both given at 100 $\mu$g/100 BW).

Various peptides in accordance with the invention were prepared in accordance with the solid phase methodology described above. The composition of the peptides is reported hereinbelow in Table I.

TABLE I

Peptide

Control (Somatostatin)

H—Ala—Gly—Cys—Lys—Asn—Phe—Phe—Trp—Lys—Thr—Phe—Thr—Ser—Cys—OH
    1    2    3    4    5    6    7    8    9   10   11   12   13   14

Peptides of the Invention

The following peptides are bridged and have the structure:

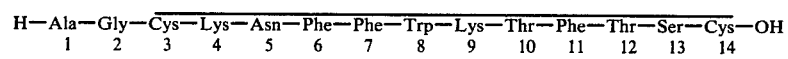

TABLE I-continued

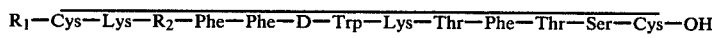
$R_1$—Cys—Lys—$R_2$—Phe—Phe—D—Trp—Lys—Thr—Phe—Thr—Ser—Cys—OH

| | $R_1$ | $R_2$ |
|---|---|---|
| 1 | H—Ala—Gly | Asn |
| 2 | H—Ala—D—Ala | Ala |
| 3 | H—Ala—Gly | Asn |
| 4 | H—Ala | Ala |
| 5 | H—Ala—Gly | Ala |
| 6 | des—Ala—Gly | Ala |
| 7 | H—Ala—D—Ala | Asn |
| 8 | H—Tyr—Gly | " |
| 9 | H—Gly—Gly—Gly—Ala—Gly | " |
| 10 | " | Ala |
| 11 | H—Gly—Gly—Gly—Ala—Ala | Ala |
| 12 | " | Asn |
| 13 | —Gly—Gly—Gly—Ala—D—Ala | " |
| 14 | " | Ala |
| 15 | H—Ala—Gly | des—Asn |

The potency of somatostatin (control) and of the peptides of the invention to inhibit secretion of growth hormone were determined by the in vitro test described above. Each of the peptides of the invention described in Table I were 8 to 10 times more effective than the somatostatin control to inhibit secretion of growth hormone. The relative potency value of the peptides of the invention described in Table I to inhibit arginine induced secretion of glucagon and insulin was also determined. Each of the peptides of the invention were 8 to 10 times more effective than somatostatin to inhibit arginine induced secretion of glucagon and insulin.

Various other peptides in accordance with the invention were prepared with structures identical to those set forth in Table I with the exception that Tyr was substituted for Phe at either or both of the 7 and 11 positions. These Tyr substituted peptides also had potency in respect to growth hormone, glucagon, and insulin inhibition of at least 8 times that of somatostatin.

Linear counterparts to the peptides of the invention set forth in Table I were also synthesized. Such linear peptides also had potency in respect to growth hormone, glucagon, and insulin inhibition of at least 8 times that of somatostatin.

Relative potency values (Somatostatin = 100%) for a series of peptides of the invention on inhibition of growth hormone secretion and inhibition of insulin and glucagon induced by arginine are shown in Table II.

TABLE II

Relative potency values of somatostatin (SRIF) and substituted somatostatin in respect to inhibition of growth hormone (GH) release from anterior pituitary cells in vitro and the inhibition of insulin and glucagon release inducted by arginine in vivo. For the in vivo determinations, the peptides were administered by injection into the jugular vein immediately prior to arginine injection (100 mg/100 g BW)

| Peptide | GH | Insulin | Glucagon |
|---|---|---|---|
| SRIF | 100 | 100 | 100 |
| Ala$^2$SRIF | 190 | 135 | 279 |
| D-Ala$^2$SRIF | 103 | 227 | 240 |
| Ala$^5$SRIF | 130 | 132 | — |
| Ala$^6$SRIF | 1 | <10 | — |
| Ala$^7$SRIF | 3 | <10 | — |
| Ala$^8$SRIF | <0.5 | <10 | — |
| Ala$^{10}$SRIF | 25 | 14 | — |
| Ala$^{11}$SRIF | 2 | <10 | — |
| Ala$^{12}$SRIF | 4 | 26 | — |
| Ala$^{13}$SRIF | 6 | 27 | — |

What is claimed is:

1. A pharmaceutically active compound, said compound being a peptide selected from the group consisting of $R_1$-Cys-Lys-$R_2$-Phe-Phe-D-Trp-Lys-Thr-Phe-Thr-Ser-Cys-OH, and $R_1$-Cys-Lys-$R_2$-Phe-Phe-D-Trp-Lys-Thr-Phe-Thr-Ser-Cys-OH, where $R_1$ is an acyl group derived from the group consisting of amino acids, dipeptides, tripeptides, pentapeptides, aliphatic, aromatic and cyclic organic acids having from 1 to 10 carbon atoms or hydrogen and $R_2$ is selected from Ala and Asn.

2. A compound in accordance with claim 1 wherein $R_1$ is an amino acid.

3. A compound in accordance with claim 1 wherein $R_1$ is a dipeptide.

4. A compound in accordance with claim 1 wherein $R_1$ is a tripeptide.

5. A compound in accordance with claim 1 wherein $R_1$ is a pentapeptide.

6. A compound in accordance with claim 1 wherein $R_1$ is an aromatic acid having not more than 10 carbon atoms.

7. A compound in accordance with claim 1 wherein $R_1$ is a cyclic organic acid having not more than 10 carbon atoms.

8. A compound in accordance with claim 1 wherein $R_1$ is selected from the group consisting of Gly, Ala, Ala-Gly, Acetyl-Ala-Gly, des Ala-Gly-des amino Cys, Tyr-Gly, Sarc-Gly, Tyr-Ala-Gly, Ala-Tyr-Gly, Gly-Gly-Gly-Ala-Gly, Gly-Gly-Gly-Ala-Ala, Gly-Gly-Gly-Ala-D-Ala, Acetyl, Acryl, Pivalyl, and Benzoyl.

9. A compound in accordance with claim 8 wherein $R_2$ is Ala.

10. A compound in accordance with claim 8 wherein $R_2$ is Asn.

11. A compound in accordance with claim 8 wherein $R_1$ is Gly.

12. A compound in accordance with claim 8 wherein $R_1$ is Ala.

13. A compound in accordance with claim 8 wherein $R_1$ is D-Ala.

14. A compound in accordance with claim 8 wherein $R_1$ is Ala-Gly.

15. A compound in accordance with claim 8 wherein $R_1$ is Acetyl-Ala-Gly.

16. A compound in accordance with claim 8 wherein $R_1$ is Tyr-Gly.

17. A compound in accordance with claim 8 wherein $R_1$ is Sarc-Gly.

18. A compound in accordance with claim 8 wherein $R_1$ is Tyr-Ala-Gly.

19. A compound in accordance with claim 8 wherein $R_1$ is Ala-Tyr-Gly.

20. A compound in accordance with claim 8 wherein $R_1$ is Acetyl.

21. A compound in accordance with claim 8 wherein $R_1$ is Acryl.

22. A compound in accordance with claim 8 wherein $R_1$ is Pivalyl.

23. A compound in accordance with claim 8 wherein $R_1$ is Benzoyl.

24. A compound in accordance with claim 8 wherein any Ala connected to $Cys^3$ is the D isomer.

25. A compound in accordance with claim 1 wherein $R_2$ is Ala.

26. A compound in accordance with claim 1 wherein $R_2$ is D-Ala.

27. A compound in accordance with claim 1 wherein $R_1$ is Ala-Gly, $R_2$ is Asn and Ala is substituted for $Cys^3$.

28. A compound in accordance with claim 1 wherein $R_1$ is Ala-Gly, $R_2$ is Asn and Ala is substituted for $Lys^4$.

29. A compound in accordance with claim 1 wherein $R_1$ is Ala-Gly, $R_2$ is Asn, and Ala is substituted for $Phe^6$.

30. A compound in accordance with claim 1 wherein $R_1$ is Ala-Gly, $R_2$ is Asn, and Ala is substituted for $Phe^7$.

31. A compound in accordance with claim 1 wherein $R_1$ is Ala-Gly, $R_2$ is Asn, and Ala is substituted for $Lys^9$.

32. A compound in accordance with claim 1 wherein $R_1$ is Ala-Gly, $R_2$ is Asn, and Ala is substituted for $Thr^{10}$.

33. A compound in accordance with claim 1 wherein $R_1$ is Ala-Gly, $R_2$ is Asn, and Ala is substituted for $Phe^{11}$.

34. A compound in accordance with claim 1 wherein $R_1$ is Ala-Gly, $R_2$ is Asn, and Ala is substituted for $Thr^{12}$.

35. A compound in accordance with claim 1 wherein $R_1$ is Ala-Gly, $R_2$ is Asn, and Ala is substituted for $Ser^{13}$.

36. A compound in accordance with claim 1 wherein $R_1$ is Ala-Gly, $R_2$ is Asn, and Ala is substituted for $Cys^{14}$.

37. A compound in accordance with claim 1 wherein $R_1$ is Ala-Gly, $R_2$ is Asn, and Ala is substituted for $Cys^3$ and $Cys^{14}$.

38. A composition in accordance with claim 1 wherein Ala is substituted for D-Trp.

39. $D-Trp^8$ somatostatin having the formula:

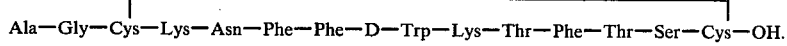

40. $Ala^5$, $D-Trp^8$ somatostatin having the formula:

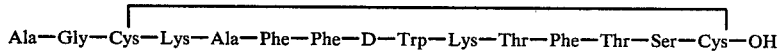

41. $D-Ala^2$, $D-Trp^8$ somatostatin having the formula:

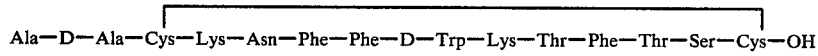

42. $D-Ala^2$, $Ala^5$, $D-Trp^8$ somatostatin having the formula:

* * * * *

UNITED STATES PATENT AND TRADEMARK OFFICE
CERTIFICATE OF CORRECTION

PATENT NO. : 4,372,884
DATED : February 8, 1983
INVENTOR(S) : Brown, Rivier and Vale, Jr.

It is certified that error appears in the above-identified patent and that said Letters Patent is hereby corrected as shown below:

Column 1, line 3, as the first paragraph, insert:

"The invention described herein was made in the course of work under a grant or award from the Department of Health and Human Services (formerly DHEW)".

Column 3, line 63, change "$N_{60}$" to --$N^{\alpha}$--.

Column 6, line 15, change "assey" to --assay--.

Column 7, line 16, change "-Gly-Gly-Gly-Ala-D-Ala" to --H-Gly-Gly-Gly-Ala-D-Ala--.

Signed and Sealed this

Seventeenth Day of May 1983

[SEAL]

Attest:

DONALD J. QUIGG

Attesting Officer     Acting Commissioner of Patents and Trademarks